(12) United States Patent
Yamasaki et al.

(10) Patent No.: US 10,859,553 B2
(45) Date of Patent: Dec. 8, 2020

(54) IDENTIFICATION APPARATUS AND IDENTIFICATION SYSTEM

(71) Applicant: KYOCERA Corporation, Kyoto (JP)

(72) Inventors: Hirohide Yamasaki, Yokohama (JP); Shinichi Kobori, Saitama (JP)

(73) Assignee: KYOCERA Corporation, Kyoto (JP)

( * ) Notice: Subject to any disclaimer, the term of this patent is extended or adjusted under 35 U.S.C. 154(b) by 79 days.

(21) Appl. No.: 16/079,465

(22) PCT Filed: Feb. 17, 2017

(86) PCT No.: PCT/JP2017/005968
§ 371 (c)(1),
(2) Date: Aug. 23, 2018

(87) PCT Pub. No.: WO2017/145944
PCT Pub. Date: Aug. 31, 2017

(65) Prior Publication Data
US 2019/0041375 A1 Feb. 7, 2019

(30) Foreign Application Priority Data

Feb. 26, 2016 (JP) ................. 2016-036230

(51) Int. Cl.
*G01N 33/03* (2006.01)
*A23L 5/10* (2016.01)
*A47J 37/12* (2006.01)

(52) U.S. Cl.
CPC ............. *G01N 33/03* (2013.01); *A23L 5/10* (2016.08); *A47J 37/1266* (2013.01); *A47J 37/1276* (2013.01)

(58) Field of Classification Search
None
See application file for complete search history.

(56) References Cited

U.S. PATENT DOCUMENTS

| | | | |
|---|---|---|---|
| 6,777,009 B1 * | 8/2004 | Shealy | A47J 37/1266 426/231 |
| 7,504,836 B2 * | 3/2009 | Chambon | A47J 37/1266 324/686 |
| 7,885,521 B2 | 2/2011 | Feinberg et al. | |
| 8,111,979 B2 | 2/2012 | Feinberg et al. | |
| 8,497,691 B2 * | 7/2013 | Behle | A47J 37/1223 324/698 |

(Continued)

FOREIGN PATENT DOCUMENTS

| | | |
|---|---|---|
| JP | H06-178731 A | 6/1994 |
| JP | 2004-008255 A | 1/2004 |

(Continued)

OTHER PUBLICATIONS

Yoshihiro Tanaka; Electric dust collecting device and electric dust collecting unit integrated with fryer; Jun. 11, 2015, JP 2015-107439 A (Year: 2015).*

*Primary Examiner* — Nasima Monsur
(74) *Attorney, Agent, or Firm* — Studebaker & Brackett PC

(57) ABSTRACT

An identification apparatus for identifying a degree of degradation of oil, including a sensor configured to detect a substance arising from oil contained in an oil tank, and a controller configured to determine a degree of degradation of the oil based on information related to the substance detected by the sensor and a type of food that is cooked with the oil.

6 Claims, 4 Drawing Sheets

(56) References Cited

U.S. PATENT DOCUMENTS

2008/0213445 A1* 9/2008 Feinberg ............ A47J 37/1223
426/417
2011/0129578 A1 6/2011 Feinberg et al.

FOREIGN PATENT DOCUMENTS

JP 2013-154227 A 8/2013
JP 2015-107439 A 6/2015

* cited by examiner

IDENTIFICATION APPARATUS AND IDENTIFICATION SYSTEM

CROSS REFERENCE TO RELATED APPLICATION

The present application claims priority to and the benefit of Japanese Patent Application No. 2016-036230 filed on Feb. 26, 2016, the entire contents of which are incorporated herein by reference.

TECHNICAL FIELD

This disclosure relates to an identification apparatus and an identification system that identify the degree of oil degradation.

BACKGROUND

When cooking oil contained in an oil tank is heated to fry food multiple times, the cooking oil gradually degrades. An apparatus that can objectively judge the time for replacement of cooking oil in accordance with the degradation of the cooking oil has been proposed.

SUMMARY

An identification apparatus according to an embodiment of this disclosure identifies the degree of oil degradation. The identification apparatus includes a sensor configured to detect a substance arising from oil contained in an oil tank, and a controller configured to determine a degree of degradation of the oil based on information related to the substance detected by the sensor and a type of food that is cooked with the oil.

This disclosure may also be implemented as a system substantially corresponding to the above-described identification apparatus. Such a system is to be understood as included in the scope of this disclosure.

For example, an identification system according to an embodiment of this disclosure includes a detection apparatus and an identification apparatus. The detection apparatus includes a sensor configured to detect a substance arising from oil contained in an oil tank and a communication interface configured to transmit information related to the substance detected by the sensor. The identification apparatus includes a communication interface configured to receive the information over a network and a controller configured to determine a degree of degradation of the oil based on the information and a type of food that is cooked with the oil.

DETAILED DESCRIPTION

Conventional apparatuses use an oil tank that is formed integrally with the identification apparatus. In either case, degradation of cooking oil cannot be identified without attaching the identification apparatus to the oil tank. According to the identification apparatus and identification system of this disclosure, it is possible to identify the degree of oil degradation without attachment to an oil tank.

The following describes an embodiment in detail with reference to the drawings.

Embodiment 1

Figure 1:
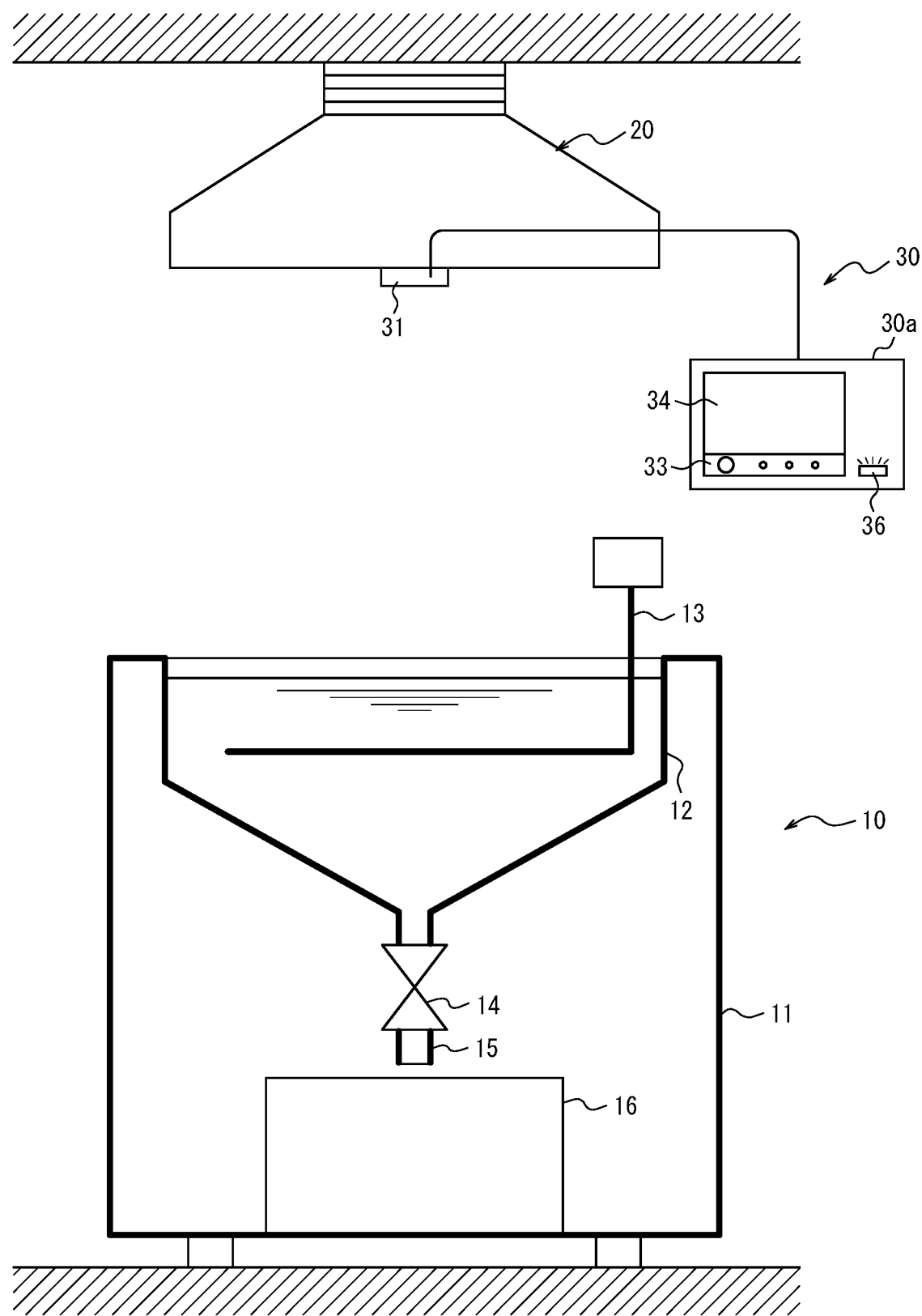
FIG. 1 schematically illustrates an example of placement of an identification apparatus according to an embodiment of this disclosure.

FIG. 1 schematically illustrates an example of placement of an identification apparatus according to Embodiment 1. The following describes the case of the oil being cooking oil, but this example is not limiting. The oil may, for example, be a different type of oil such as oil for fuel or industrial oil.

In FIG. 1, a fryer 10 for cooking fried food such as tempura or fried chicken is installed on the floor. The fryer 10 includes a box-shaped cabinet 11 and an oil tank 12 that contains cooking oil in the upper portion of the cabinet 11. The cooking oil contained inside the oil tank 12 is heated by a heater 13. An oil drain pipe 15 is connected to the bottom of the oil tank 12 via a valve 14. To facilitate oil drainage, the bottom of the oil tank 12 is inclined downwards towards the valve 14 and the oil drain pipe 15. Cooking oil that has degraded is discharged as waste oil by opening the valve 14. A waste oil tank 16 is disposed at the bottom of the oil drain pipe 15 in order to collect the discharged waste oil.

As illustrated in FIG. 1, the oil tank 12 is envisioned as being installed in a large-scale fryer 10 used in, for example, a convenience store or a restaurant, but not limited to these examples. The oil tank 12 may be installed in a smaller scale fryer. In addition to being installed in a fryer, the oil tank 12 may, for example, be installed in a cookware for fried food used at home.

Cooking exhaust, such as water vapor and oily smoke, is generated as a result of frying. In order to discharge the generated cooking exhaust sufficiently to the outside, an exhaust fan 20 is installed above the oil tank 12.

Figure 2:
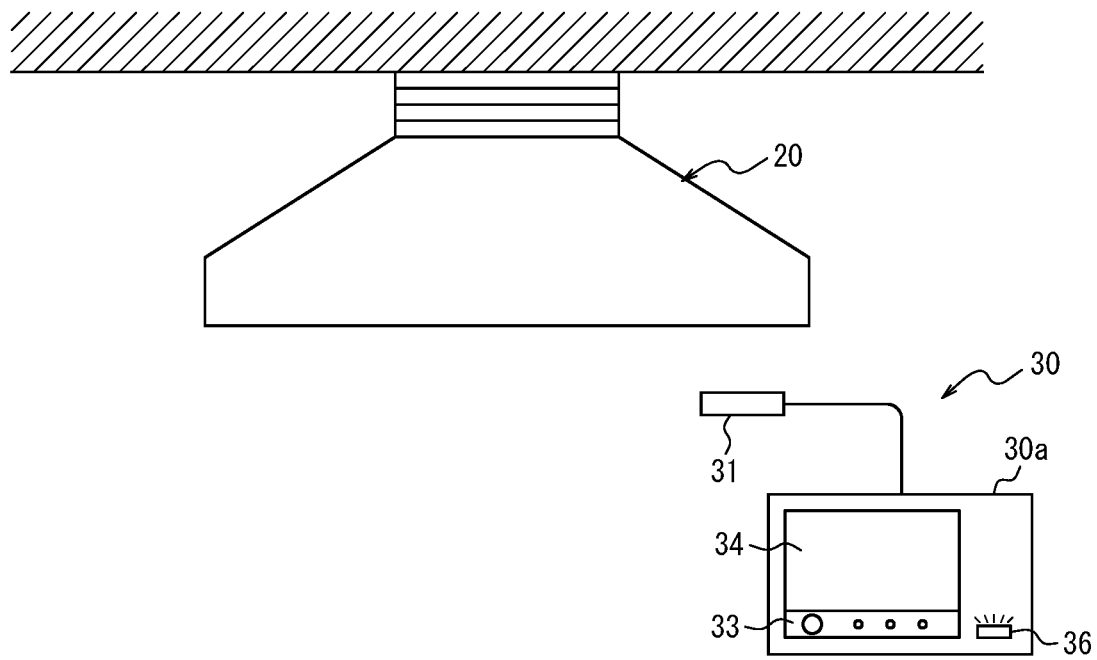
FIG. 2 schematically illustrates another example of placement of the identification apparatus in FIG. 1.

An identification apparatus 30 according to an embodiment, for example, includes a main body 30a and a sensor 31. The main body 30a may, for example, be disposed on a wall adjacent to the ceiling where the exhaust fan 20 is installed so that the user can operate the main body 30a. The sensor 31 may, for example, be disposed in the exhaust fan 20. As illustrated in FIG. 2, the sensor 31 may be disposed near the exhaust fan 20 instead. "Near the exhaust fan 20" may, for example, refer to a wall adjacent to the ceiling where the exhaust fan 20 is installed.

Figure 3:
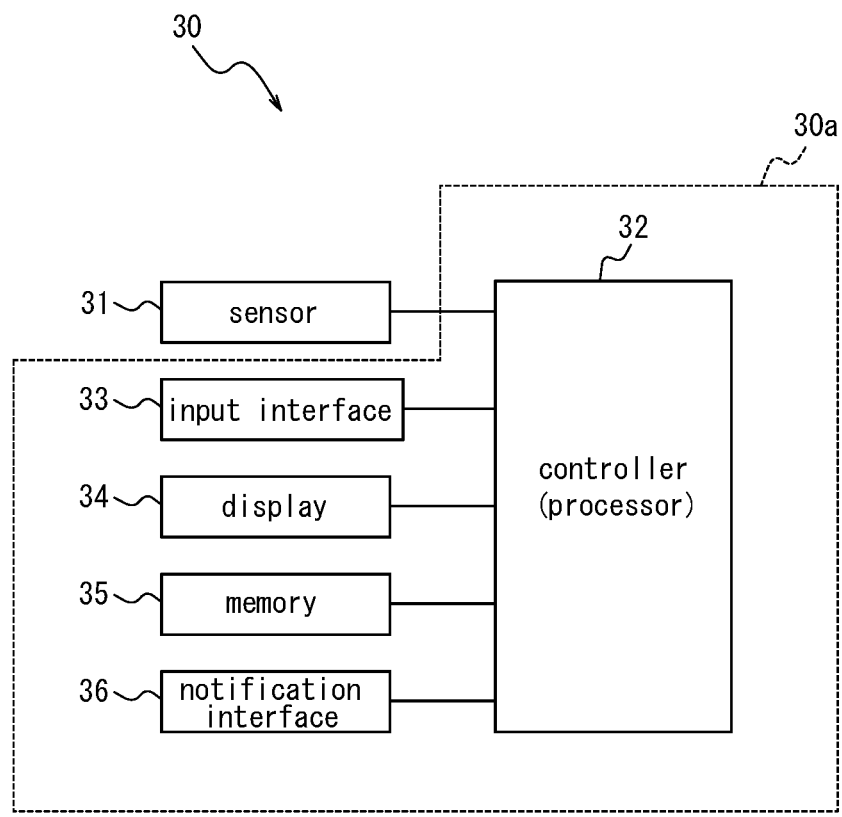
FIG. 3 is a functional block diagram schematically illustrating the structure of the identification apparatus in FIG. 1.

FIG. 3 is a functional block diagram schematically illustrating the structure of an identification apparatus 30 according to an embodiment. The identification apparatus 30 includes a sensor 31, a controller 32, an input interface 33, a display 34, a memory 35, and a notification interface 36.

The sensor 31 detects a substance arising from cooking oil contained in the oil tank 12. The actual sensor configuring the sensor 31 may be any sensor that can detect the substance. For example, it may be a sensor that detects an odor arising from the cooking oil. In other words, the sensor that configures the sensor 31 includes a sensitive membrane and a transducer, where the sensitive membrane adsorbs gas molecules that are the source of the odor, and the transducer converts the gas molecules in the sensitive membrane into an electrical signal. The sensor 31 transmits the electrical signal converted by the transducer to the controller 32. For example, if the cooking oil degrades, then fatty acids included in the cooking oil decompose. Upon fatty acids decomposing, aldehyde-based or ketone-based substances are generated. In other words, for the sensor 31 to detect the degree of degradation of cooking oil, it suffices, for example, to provide a sensitive membrane that can detect aldehyde-based or ketone-based substances.

The sensor 31 may, for example, be provided with a Quartz Crystal Microbalance type odor sensor that includes a quartz crystal and a sensitive membrane made of an organic thin film. The Quartz Crystal Microbalance type odor sensor detects an odor by the resonance frequency of the quartz crystal changing upon gas molecules being adsorbed on the sensitive membrane. The quartz crystal functions as a transducer that converts detection of gas molecules into an electric signal.

The sensor 31 may, for example, be provided with an oxide semiconductor gas sensor. The oxide semiconductor gas sensor detects the gas concentration by a change in the resistance of an oxide semiconductor after gas molecules are adsorbed on the oxide semiconductor. The oxide semiconductor functions as a transducer that converts detection of gas molecules into an electric signal. The sensor 31 may, for example, be provided with a sensor such as an infrared gas sensor, an electrochemical gas sensor, a contact combustion type gas sensor, or a biosensor.

The controller 32 is a processor that, starting with the functional blocks of the identification apparatus 30, controls and manages the identification apparatus 30 overall. The controller 32 is configured using a processor such as a Central Processing Unit (CPU) that executes a program prescribing control procedures. Such a program may, for example, be stored in the memory 35 or in an external storage medium.

The identification apparatus 30 includes a controller 32 including at least one processor for providing control and processing capability to perform various functions as described in further detail below. In accordance with various embodiments, the at least one processor may be implemented as a single integrated circuit or as multiple communicatively coupled integrated circuits and/or discrete circuits. It is appreciated that the at least one processor can be implemented in accordance with various known technologies. In one embodiment, the processor includes one or more circuits or units configurable to perform one or more data computing procedures or processes by executing instructions stored in an associated memory, for example. In another embodiment, the processor may be implemented as firmware (e.g. discrete logic components) configured to perform one or more data computing procedures or processes. In accordance with various embodiments, the processor may include one or more processors, controllers, microprocessors, microcontrollers, application specific integrated circuits, digital signal processors, programmable logic devices, field programmable gate arrays, or any combination of these devices or structures, or combination of other known devices and structures, to perform the functions described below.

The controller 32 displays types of food on the display 34 based on an operation on the input interface 33 by the user. The types of food may, for example, be displayed as a list of menu only in characters. The types of food may, for example, be displayed one by one on the entire display 34 in a form of combination of characters and other elements such as photographs or picture patterns. The data related to the types of food may, for example, be stored in the memory 35 or in an external storage medium. The user selects food that is to be fried in the oil tank 12 from the foods displayed on the display 34, and then the controller 32 acquires information related to the selected food from the input interface 33. The controller 32 may, for example, determine the type of food based on information related to the odor detected by the sensor 31 during frying.

The controller 32 executes identification processing by the identification apparatus 30 by controlling the entire identification apparatus 30. For example, the controller 32 activates the sensor 31 based on a predetermined input operation to the identification apparatus 30 by the user of the identification apparatus 30. The "predetermined input operation" described here may, for example, refer to an operation to turn on the power of the identification apparatus 30, or an operation to select the type of food to be fried. The sensor 31 activated by the controller 32 starts to detect an odor arising from the cooking oil. The controller 32 acquires information related to the odor detected by the sensor 31 from the sensor 31.

The controller 32 determines the degree of degradation of the cooking oil based, for example, on information related to the odor detected by the sensor 31 during frying and on the type of food that is cooked with the cooking oil. The odor arising from the cooking oil contained in the oil tank 12 during cooking changes depending on the type of food that is cooked. The optimum time for replacement of cooking oil differs for each type of food that is cooked. For example, it is known from experience that, in the case of tempura, using fresher cooking oil makes the cooked tempura more delicious. In the case of fried chicken, however, using cooking oil that has been used and degraded to some extent makes the cooked fried chicken have a richer and more delicious taste. In this way, the degradation state of cooking oil acceptable for each food is different. Therefore, it is preferable that the controller 32 determines a criterion for judging the degradation of cooking oil for each type of food and then identifies the degree of degradation of the cooking oil. The controller 32 checks the information related to the odor detected by the sensor 31 against data that, based on the type of food, indicate the correlation between the odor arising from cooking oil and the degree of degradation of the cooking oil. The data may, for example, be stored in advance in the memory 35. When checking, the controller 32 acquires the data from the memory 35 and executes the processing for checking. As a result, the identification apparatus 30 can identify the degree of degradation of the cooking oil. The information related to the odor detected by the sensor 31 is not limited to an odor arising during frying and may be an odor arising while not cooking.

The controller 32 may, for example, determine the degree of degradation of the cooking oil based on the outputs of a plurality of sensors and the ratio of the outputs. For example, the controller 32 may determine the degree of degradation of the cooking oil based on characteristic values (such as output value, or time constant) of the response of a plurality of sensors. For example, the identification apparatus 30 may include a plurality of sensors configured to detect odors such as ethylene odors, alcohol odors, sulfur odors, ammonia odors, aldehyde odors, or ketone odors. When determining the degree of degradation of the cooking oil, for example, the controller 32 may determine that the cooking oil has degraded when, among the outputs of the plurality of sensors, the outputs from sensors that detect aldehyde odors or ketone odors have exceeded a predetermined threshold.

The controller 32 may, for example, determine the type of food based on the outputs of a plurality of sensors and the ratio of the outputs. For example, the controller 32 may determine the type of food based on characteristic values (such as output value, or time constant) of the response of a plurality of sensors. For example, the identification apparatus 30 may determine the type of food based on the degree of matching between the characteristic values of the response of the plurality of sensors stored for each type of food in advance and the data detected by the plurality of sensors.

When determining that, based on the type of food, the degree of degradation of the cooking oil has exceeded a predetermined threshold, the controller 32 controls the notification interface 36 to notify the user. This threshold may be set for each type of food in advance based on data that are stored in advance in the memory 35 and indicate the correlation between an odor arising from the cooking oil and the degree of degradation of the cooking oil. The threshold may be changed appropriately by the user. In either case, the controller 32 stores information related to the threshold in the memory 35.

The controller 32 may determine the degree of degradation of cooking oil using a statistical method such as principal component analysis, or using a neural network. The controller 32 may generate data by performing a learning process in advance to extract the characteristic values of the response of a plurality of sensors for each degradation state of cooking oil. The data may be generated for each type of food. The controller 32 may store the data after learning in the memory 35. The controller 32 may then determine the degree of degradation of cooking oil based on the degree of matching between the data after learning that are stored in the memory 35 and the data that are detected by the plurality of sensors. Based on newly detected data, the controller 32 may update the data after learning that are stored in the memory 35.

The input interface 33 receives an input operation from the user. The input interface 33 may, for example, be configured by operation buttons or operation keys. The input interface 33 is not limited to such a configuration, and may be configured by a touch screen. In this case, the input interface 33 may be an input area, for receiving operations input by the user, displayed on a part of the display 34 and receive touching operations input by the user. Before the identification apparatus 30 executes the identification processing, the input interface 33 receives a predetermined input operation from the user. The input interface 33 transmits a signal based on the input operation of the user to the controller 32.

The display 34 displays various items for the user to perform an input operation. For example, when the user selects a type of food to be fried, the display 34 receives a control signal from the controller 32 and displays types of food based on the data related to the types of food that are stored in the memory 35. For example, when the notification interface 36 notifies the user of the degree of degradation of the cooking oil, the display 34 may serve as an auxiliary role to the notification from the notification interface 36 and display that it is necessary to replace the cooking oil.

The memory 35 may, for example, be configured by a semiconductor memory or a magnetic memory. The memory 35 may, for example, store a variety of information and programs for causing the identification apparatus 30 to operate. The memory 35 also functions as a working memory. The memory 35 stores data related to the type of food to be fried. The memory 35 stores data that, for each type of food to be fried, indicate the correlation between the odor arising from cooking oil and the degree of degradation of the cooking oil. The memory 35 stores information related to different thresholds for each type of food to be fried.

When the controller 32 determines that the degree of degradation of the cooking oil has exceeded a predetermined threshold, the notification interface 36 notifies the user. The notification interface 36 can provide notification, for example, by a visual method such as one using image, character, or color display, or light emission; an auditory method such as one using audio; or a combination of these methods. In the case of providing notification with a visual method, the notification interface 36 may, for example, be used in combination with the display 34, or be configured by a different display device. In this case, the notification interface 36 may provide notification by displaying images or characters. As illustrated in FIG. 1, the notification interface 36 may, for example, provide notification by causing a light emitting device such as an LED to emit light. In the case of providing notification with an auditory method, the notification interface 36 may, for example, be configured by a sound generating device such as a speaker that provides notification by outputting, for example, an alarm sound or audio guidance. Provision of notification by the notification interface 36 is not limited to a visual or auditory method. Any method by which the user can objectively recognize the time for replacement of cooking oil may be adopted. For example, the notification interface 36 may provide notification with a different method such as a vibration pattern.

Figure 4:
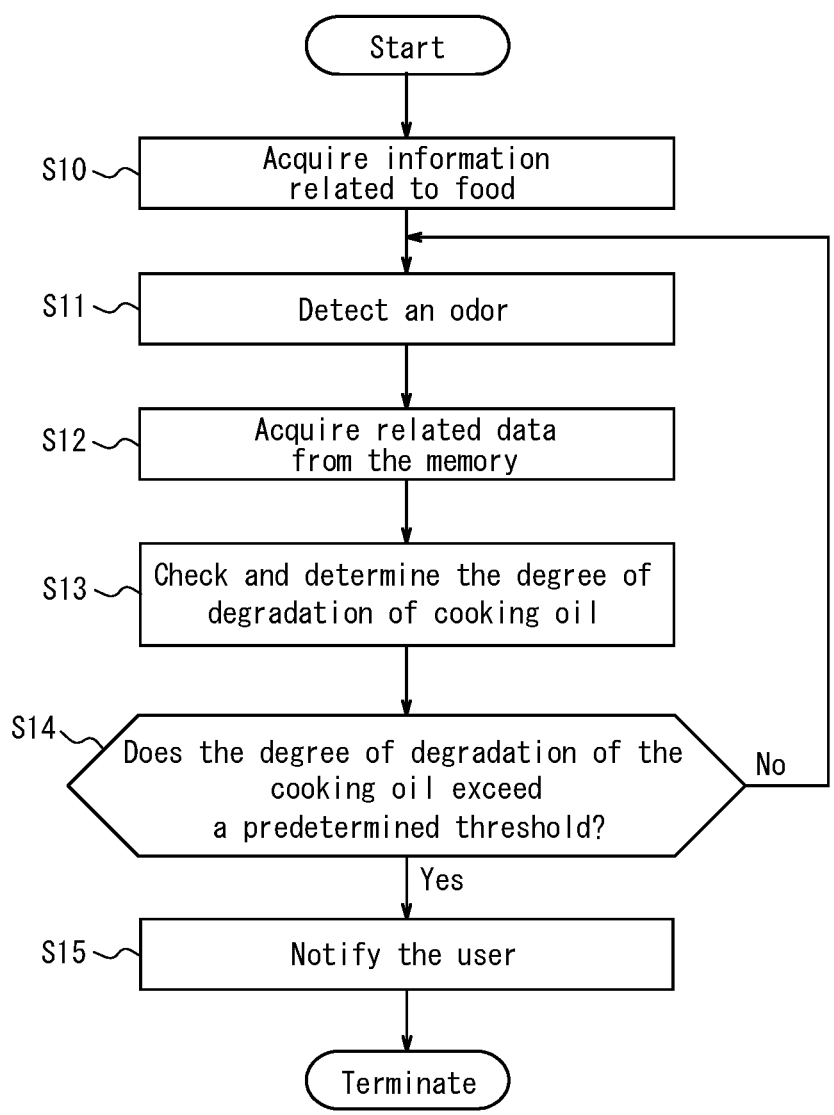
FIG. 4 is a flowchart illustrating the operation of the identification apparatus in FIG. 1.

FIG. 4 is a flowchart illustrating the operation of an identification apparatus 30 according to an embodiment.

The user performs a predetermined input operation to the input interface 33 so that the identification apparatus 30 starts the identification processing. For example, the user selects a type of food to be cooked and then starts cooking using heated cooking oil.

After the identification apparatus 30 starts the identification processing, the controller 32 acquires information related to the food from the input interface 33 (step S10).

The controller 32 activates the sensor 31 and detects an odor arising from the cooking oil contained in the oil tank 12 (step S11).

From the memory 35, the controller 32 acquires data indicating the correlation among the type of food being fried, the odor, and the degree of degradation of the cooking oil (step S12). In other words, the controller 32 acquires data indicating the correlation between the odor and the degree of degradation of the cooking oil based on the food being fried.

The controller 32 checks the information related to the odor detected by the sensor 31 against the data, acquired from the memory 35, that indicate the correlation and determines the degree of degradation of the cooking oil (step S13).

The controller 32 determines whether the degree of degradation of the cooking oil exceeds a predetermined threshold (step S14). When the predetermined threshold is exceeded, processing proceeds to step S15. When the predetermined threshold is not exceeded, processing returns to step S11.

When the controller 32 determines that the degree of degradation of the cooking oil has exceeded a predetermined threshold, the controller 32 controls the notification interface 36. As a result, the notification interface 36 notifies the user (step S15). The processing flow then terminates.

An identification apparatus 30 according to an embodiment can identify the degree of degradation of cooking oil without attachment to an oil tank 12.

An identification apparatus 30 according to an embodiment identifies the degree of degradation of cooking oil based on an odor detected by a sensor 31. Therefore, the user can objectively perceive the degradation of cooking oil. In other words, the user can objectively learn the time for replacement of cooking oil.

An identification apparatus 30 according to an embodiment disposes constituent elements including a sensor 31 on the outside of an oil tank 12. Therefore, the identification apparatus 30 is less prone to being soiled by oil and is easier to clean and manage.

An identification apparatus 30 according to an embodiment disposes constituent elements including a sensor 31 on the outside of an oil tank 12. Therefore, the identification apparatus 30 is less affected by heat, thus reducing the occurrence of failure or malfunction.

In an identification apparatus 30 according to an embodiment, a controller 32 determines the degree of degradation of cooking oil based on a type of food to be fried. Therefore, the degree of degradation of the cooking oil can be identified accurately for each type of food. In other words, the user is able to learn the time for replacement of cooking oil optimum for each food and cook food with cooking oil in an optimum state.

The identification apparatus 30 according to the above embodiment has been described as including a sensor 31 that detects an odor and a controller 32 that determines the degree of degradation of cooking oil. Different apparatuses that can communicate with each other, however, may respectively include a functional unit that detects an odor and a functional unit that determines the degree of degradation of cooking oil. The configuration in such a case is described as Embodiment 2 with reference to FIG. 5.

Embodiment 2

Figure 5:
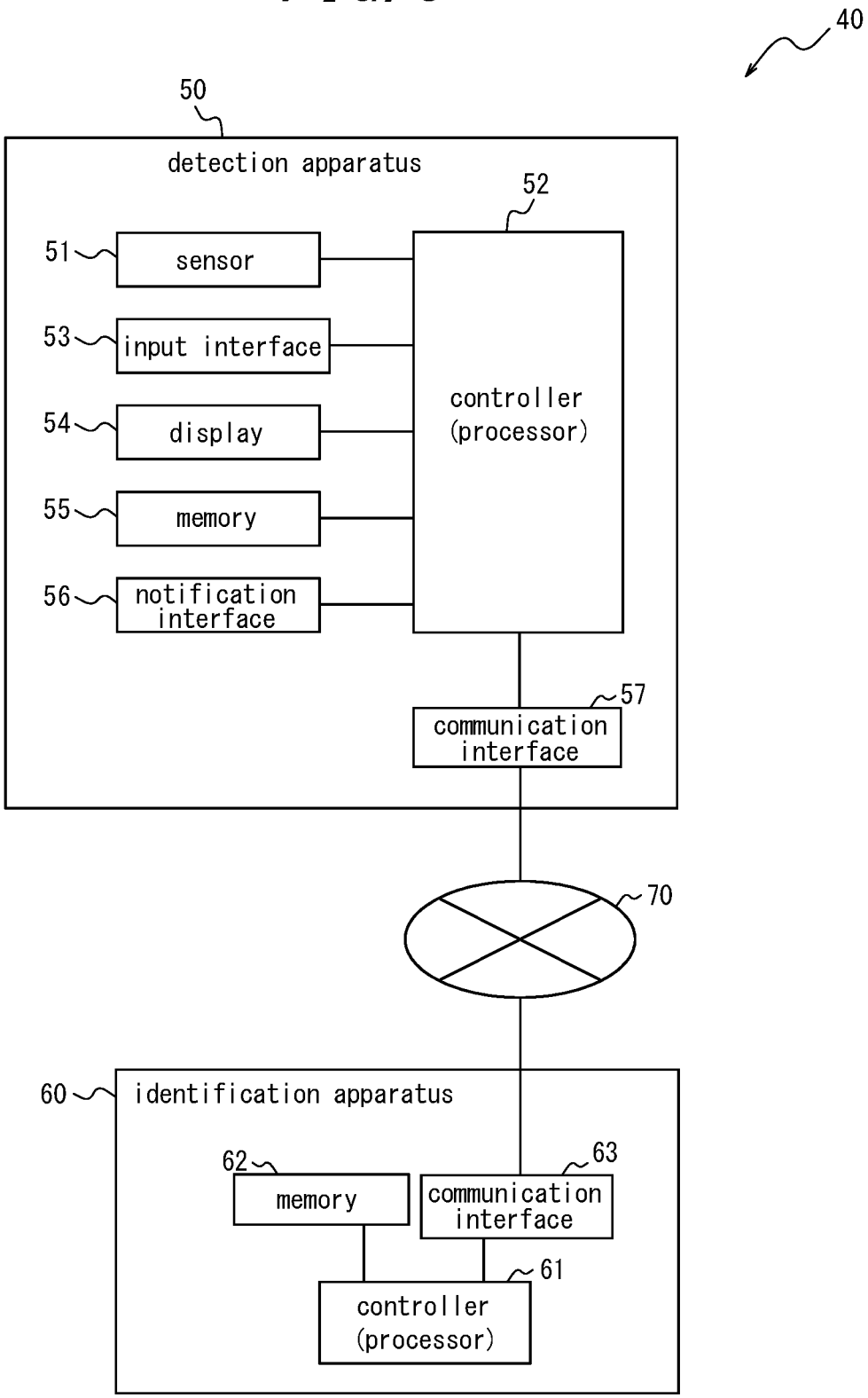
FIG. 5 is a functional block diagram schematically illustrating the structure of an identification system according to an embodiment of this disclosure.

FIG. 5 is a functional block diagram schematically illustrating the structure of an identification system 40 according to Embodiment 2. The identification system 40 includes a detection apparatus 50 and an identification apparatus 60. The detection apparatus 50 and the identification apparatus 60 are connected over a wired or wireless network 70, such as an Internet connection, a Wide Area Network (WAN), or a Local Area Network (LAN), for communication with each other.

The detection apparatus 50 is placed in the same way as the identification apparatus 30 according to Embodiment 1 as illustrated in FIG. 1 or 2. The detection apparatus 50 includes a sensor 51, a controller 52, an input interface 53, a display 54, a memory 55, a notification interface 56, and a communication interface 57. The functions of the sensor 51, controller 52, input interface 53, display 54, memory 55, and notification interface 56 are similar to the functions of the sensor 31, controller 32, input interface 33, display 34, memory 35, and notification interface 36 of the identification apparatus 30 as illustrated in FIG. 3. Hence, a description thereof is omitted here. The remaining structure, placement, and the like are also identical to those of the identification apparatus 30 according to Embodiment 1. Hence, a description thereof is omitted, and the following focuses mainly on the differences from Embodiment 1.

A controller 52 of a detection apparatus 50 according to an embodiment does not determine the degree of degradation of cooking oil. Instead, via a communication interface 57 and a network 70, the controller 52 transmits information related to an odor detected by a sensor 51 to an external identification apparatus 60. Subsequently, the controller 52 acquires information, transmitted over the network 70 from the identification apparatus 60, related to the identified degree of degradation of the cooking oil via the communication interface 57. When the degree of degradation of the cooking oil exceeds a predetermined threshold, the controller 52 controls a notification interface 56 to notify the user.

By communicating with the identification apparatus 60 over the network 70, the communication interface 57 transmits and receives a variety of information.

For example, the communication interface 57 transmits information related to the odor detected by the sensor 51 to the identification apparatus 60. When the user appropriately sets a threshold related to the degree of degradation of cooking oil, the communication interface 57 also transmits information related to the set threshold to the identification apparatus 60. The communication interface 57 also transmits information related to the type of food to be fried, as selected by the user, to the identification apparatus 60. Various information transmitted from the detection apparatus 50 to the identification apparatus 60 may, for example, be transmitted each time the controller 52 acquires such information or be transmitted when the user performs a predetermined input operation on the detection apparatus 50.

The communication interface 57 acquires information related to the degree of degradation of the cooking oil, as identified by the identification apparatus 60, from the identification apparatus 60 over the network 70.

The identification apparatus 60 may, for example, be configured by a server. The identification apparatus 60 includes a controller 61, a memory 62, and a communication interface 63.

The controller 61 is a processor that, starting with the functional blocks of the identification apparatus 60, controls and manages the identification apparatus 60 overall. The controller 61 is configured using a processor such as a Central Processing Unit (CPU) that executes a program prescribing control procedures. Such a program may, for example, be stored in the memory 62 or in an external storage medium.

The controller 61 determines the degree of degradation of the cooking oil based on the various information received from the detection apparatus 50 via the communication interface 63. In other words, the controller 61 determines the degree of degradation of the cooking oil based on information related to the odor detected by the sensor 51 and on the type of food that is fried. The controller 61 checks the information related to the odor detected by the sensor 51 against data that, based on the type of food, indicate the correlation between the odor arising from the cooking oil and the degree of degradation of the cooking oil. The data may, for example, be stored in advance in the memory 62. When checking, the controller 61 acquires the data from the memory 62 and executes the processing for checking.

Based on the information related to a threshold received from the detection apparatus 50 via the communication interface 63, the controller 61 determines whether the degree of degradation of the cooking oil has exceeded the threshold. The threshold has been described as being appropriately set in the detection apparatus 50 by the user, but this example is not limiting. The threshold may be set in advance based on data that are stored in advance in the memory 62 and indicate the correlation between the odor arising from the cooking oil and the degree of degradation of the cooking oil.

The controller 61 transmits information related to the determined degree of degradation of cooking oil to the detection apparatus 50 via the communication interface 63 and the network 70.

The memory 62 may, for example, be configured by a semiconductor memory or a magnetic memory. The memory 62, for example, stores a variety of information and programs for causing the identification apparatus 60 to operate. The memory 62 also functions as a working memory. The memory 62 stores data that, based on the type of food, indicate the correlation between the odor arising from the cooking oil and the degree of degradation of the cooking oil.

By communicating with the detection apparatus 50 over the network 70, the communication interface 63 transmits and receives a variety of information.

For example, the communication interface 63 receives information related to the odor detected by the sensor 51 from the detection apparatus 50. The communication interface 63 also receives information related to the set threshold from the detection apparatus 50. The communication interface 63 also receives information related to the type of food to be fried from the detection apparatus 50.

The communication interface 63 transmits information related to the degree of degradation of the cooking oil, as identified by the identification apparatus 60, to the detection apparatus 50.

With the above processing, an identification system 40 according to an embodiment can identify the degree of degradation of cooking oil without an identification apparatus 60 being attached to an oil tank 12. Therefore, the identification system 40 can obtain the same effect as that of the identification apparatus 30 according to Embodiment 1.

In an identification system 40 according to an embodiment, data in a memory 62, which is referred to by a controller 61 of an identification apparatus 60, can be updated as necessary for the identification apparatus 60, which is a server, to detect the degree of degradation of cooking oil. As a result, the identification system 40 can identify the degree of degradation of the cooking oil based on the updated data.

It will be clear to a person of ordinary skill in the art that this disclosure may be implemented in ways other than the above embodiments without departing from the spirit or essential features thereof. Accordingly, the above explanation merely provides examples that are in no way limiting. The scope of this disclosure is to be defined by the appended claims, not by the above explanation. Among all changes, those changes that are within the range of equivalents are considered to be included within the scope of this disclosure.

For example, the functions and the like included in the various components and steps may be reordered in any logically consistent way. Furthermore, components or steps may be combined into one or divided.

For example, in FIGS. 1 and 2, the main body 30a of the identification apparatus 30 is placed, for example, on a wall adjacent to the ceiling where the exhaust fan 20 is installed. The sensor 31 is placed on or near the exhaust fan 20. However, the placement of the main body 30a and the sensor 31 is not limited to these examples. The main body 30a may, for example, be attached to the exhaust fan 20 or be placed on the floor. Similarly, the sensor 31 may be placed on a wall closer to the oil tank 12.

For example, in the above embodiments, the sensor 31 has been described as being configured by a sensor that detects an odor arising from the cooking oil, but a sensor other than an odor-detecting sensor may be used. For example, the sensor 31 may be one that detects odorless gas molecules arising from the cooking oil.

The identification apparatus 30 and the detection apparatus 50 according to the above embodiments are configured to identify an odor arising from cooking oil that has been heated to an appropriate temperature for cooking, but these examples are not limiting. For example, the identification apparatus 30 and the detection apparatus 50 may detect an odor for determining degradation before cooking oil is overheated.

The invention claimed is:

1. An identification apparatus for identifying a degree of degradation of oil, the identification apparatus comprising:
   a sensor configured to detect a substance arising from oil contained in an oil tank; and
   a controller configured to determine a predetermined threshold of oil degradation for each type of food, and determine whether a degree of degradation of the oil exceeds the determined predetermined threshold of oil degradation, based on information related to the substance detected by the sensor and a type of food that is cooked with the oil,
   wherein the sensor includes a sensitive membrane, which adsorbs gas molecules that are sources of an odor of the oil, and a transducer, which converts the gas molecules in the sensitive membrane into an electrical signal including information on the odor of the oil, and
   wherein the controller is further configured to
   acquire the information on the odor of the oil from the sensor,
   determine the type of food based on the acquired information on the odor of the oil, and
   determine whether the degree of degradation of the oil exceeds the determined predetermined threshold of oil degradation based on a correlation between the odor of the oil and the degree of degradation of the oil, the correlation is set for each type of food.

2. The identification apparatus according to claim 1, further comprising:
   a memory; wherein
   the memory stores data indicating the correlation; and
   the controller determines the degree of degradation of the oil by checking the information against the data.

3. The identification apparatus according to claim 1, further comprising:
   a notification interface; wherein
   the controller, upon making a determination based on the type of food that the degree of degradation of the oil exceeds the predetermined threshold, provides notification of the determination via the notification interface.

4. The identification apparatus according to claim 1, wherein the sensor is disposed in or near an exhaust fan installed above the oil tank.

5. An identification system comprising:
   a detection apparatus and an identification apparatus; wherein
   the detection apparatus comprises a sensor configured to detect a substance arising from oil contained in an oil tank and a communication interface configured to transmit information related to the substance detected by the sensor; and
   the identification apparatus comprises a communication interface configured to receive the information over a network and a controller configured to determine a predetermined threshold of oil degradation for each type of food, and determine whether a degree of degradation of the oil exceeds the determined predetermined threshold of oil degradation, based on the information and a type of food that is cooked with the oil, wherein the sensor includes a sensitive membrane, which adsorbs gas molecules that are sources of an odor of the oil, and a transducer, which converts the gas molecules in the sensitive membrane into an electrical signal including information on the odor of the oil, and wherein the controller is further configured to acquire the information on the odor of the oil from the sensor, determine the type of food based on the acquired information on the odor of the oil, and determine whether the degree of degradation of the oil exceeds the determined predetermined threshold of oil degradation based on a correlation between the odor of the oil and the degree of degradation of the oil, the correlation is set for each type of food.

6. The identification system according to claim 5, wherein the identification apparatus further comprises a memory;

the memory stores data indicating the correlation; and the controller determines the degree of degradation of the oil by checking the information against the data.

* * * * *